United States Patent [19]

Long et al.

[11] Patent Number: 5,085,588

[45] Date of Patent: Feb. 4, 1992

[54] BACTERIAL PROMOTERS INDUCIBLE BY PLANT EXTRACTS

[76] Inventors: Sharon R. Long, 838 La Jennifer;
John T. Mulligan, 946 VanAuken Cir., both of, Palo Alto, Calif. 94306;
Thomas T. Egelhoff, Dept. of Bio. Sci., Stanford Univ., Stanford, Calif. 94305

[21] Appl. No.: 788,911

[22] Filed: Oct. 18, 1985

[51] Int. Cl.[5] .................. C12P 21/00; C12N 15/00; C12R 1/41; C07H 15/12
[52] U.S. Cl. .................. 435/69.1; 435/71.2; 435/172.3; 435/252.2; 435/252.3; 435/320.1; 435/878; 536/27; 424/93; 935/35; 935/36; 935/41; 935/43; 935/67; 935/72; 800/205
[58] Field of Search .................. 435/172.3, 68, 317, 435/69.1, 71.2, 252.2, 252.3, 320.1, 878, 320; 536/27; 935/29, 30, 41, 56; 800/205; 424/93

[56] References Cited
PUBLICATIONS

Olson et al. (1985), "Identification of Genes . . ." Bio Technology, Feb. 1985, 143–149.
Schofield PhD Theses (1984) Australian National University Canberra, Australia, pp. 126–206.
Egelhoff et al. (1985), "Nucleotide Sequence of . . ." DNA 4: 241–248.

*Primary Examiner*—Elizabeth C. Weimar
*Assistant Examiner*—David T. Fox

[57] ABSTRACT

Novel constructs are provided containing DNA fragments comprising a Rhizobium nodulation gene divergent transcriptional initiation regulatory region. The region is responsive to plant exudate in the presence of a nod D gene product. When associated with plants, the region can control the expression of structural genes, such as agents active in protecting plants or inducing their growth.

This invention was funded at least in-part by a grant from the National Institutes of Health. The U.S. government may have certain rights in this invention.

22 Claims, 7 Drawing Sheets

```
                                                                                   75
GAC GAG GAG GTT TAG ATC TAG GCC CCT AAA ACG CAT GTC CGG CAT CCA TAT CGC AGA TCG TTA TCC AAA CAA
                                                         <·······1A
                                           <D
                                                                                   150
TCA ATT TTA CCA ATC CTT CAG AGT CCT ATT AGA GAA CCC TGA AGT TAA TGG AAT CAA GGT CCG GCG GAA AAC
                                                                                   225
TTT CAC AAG TAC AGG ATG GGT CCG AAT TTA GAG CCG TCA TCT AAG CGC TCG ACC AAC GGT CCA GCG CTA CGG TTG
                                          1B········<              2A     2B
                                                                                   300
GCG TCC CCG GTC TAA CTT GCC GGG TAC ACA CCA CTC TCG ATC GTG CTT TGA AGA AAC AAC ACA CTG GAG TTC TTA
                                                                                   375
CAT GTC CTT AAA AGT GCA GTC GAA GCT ATG CTC GGA AAA TCA GCT GGA ACC TGC AGA CCA CCA GGA GCT CTC AGA
MET Ser Leu Lys Val Gln Trp Lys Cys Trp Glu Asn Gln Leu Glu Arg Ala Asp His Gln Glu Leu Ser Glu
                                                                                   450
ATT TTT TCC AAA ATC CTA TGG GCC CAC AGG AGC GTT CCA GCG ATT TGA GGG GCC CAG TTC GGC CGG
Phe Phe Arg Lys Ser Tyr Gly Ala Phe His Ala Lys Pro Phe Glu Gly Gly Arg Ser Trp Ala Gly
                                                                                   525
CGC GAG ACC GGA ACG CCG CCG AAT TGC TTA CGA CTC CGT CGG GAT AGC AAG CCA CAT GGC GGT GTT GGG CCG TTT
Ala Arg Pro Glu Arg Arg Ala Ile Ala Tyr Asp Ser Val Gly Ile Ala Ser His MET Gly Val Leu Arg Arg Phe

CAT TAA GGT TGG TGA GAC TGA TCT CCT TGT GGC TGA ACT GGG CTT ATA CGC GGT GCC GGA TCT CGA GCC AAT
Ile Lys Val Gly Glu Thr Asp Leu Leu Val Ala Glu Leu Gly Leu Tyr Ala Val Arg Pro Asp Leu Glu Arg MET
```

```
                                                                                          615
GGC CAT CGC TCA CTC CGT CGG TCC CTC TTT GAC TCC AAC TTT CGC GAT TGG CGC GAT TGG TCT CCC ATT CGC CTT TGG GAC AGT
Gly Ile Ala His Leu Arg Arg Ser Leu Phe Asp Ser Asn Phe Arg Asp Trp Arg Ala Ile Gly Val Pro Phe Ala Phe Gly Thr Val
                                                                                                                  675

690
TCG GCA CGC CAT GCG GAA CCA CGT TGA GAG ATA TTG CCA AAA CGG TAT GGC TAG CAT TTT GAC GGG GGT TCG AGT
Arg His Ala MET Arg Asn His Val Glu Arg Ile Leu Pro Lys Arg Tyr Gly Ser Ile Leu Thr Gly Val Arg Val
                                                                                                    750

765
GCG GTC GAG CAT CCC AGA GGT GAA CCC CGA TCT CCC TTC CAC CGA CGA CCC ACT CGT GAT ATT CCC
Arg Ser Ser Ile Ala Glu Val Asn Ala Asp Leu Pro Ser Thr Arg Thr Glu Asp Pro Leu Val Val Ile Phe Pro
                                                                                                    825

840
GCT TGC ACC TCC GTT GAA CGA ATC CCC AGG TAC ATT GAT TGA ACG GAA CGG ATC GGA GCT ATG AAG CAC CTC
Val Gly Arg Pro Leu Asn Glu Trp Pro Gly Thr Leu Ile Glu Arg Asn Gly Ser Glu Leu  .  MET Lys His Leu
                                                                                                    900

915
GAT TAC ATA CAC GAG GTC CCG AGC AAC TGC GAC GAA CAT CGT AGT ATA TAC CTC ACG TTT GAC GAC
Asp Tyr Ile His Glu Val Pro Ser Asn Cys Asp Tyr Gly Thr Glu Asp Arg Ser Ile Tyr Leu Thr Phe Asp Asp
                                                                                                    975

990
GCC CCG AAT CCA CAT TGC ACA CCG GAA ATC CTC GAT GTC CTG GCT GAA TAC GGC GTC CCG GCG ACT TTC GTC
Gly Pro Asn Pro His Cys Thr Pro Glu Ile Leu Asp Val Leu Ala Glu Tyr Gly Val Pro Ala Thr Phe Val
                                                                                                    1050

1065
ATC GGC ACC TAT GCG AAA AGC CAG GAA CTC ATT CGA CGT ATC GTC GCG GAA GGT CAC GAA GTG GCT AAC CAC
Ile Gly Thr Tyr Ala Lys Ser Gln Pro Glu Leu Ile Arg Arg Ile Val Ala Glu Gly His Glu Val Ala Asn His
                                                                                                    1125
```

```
1140                                                1170                                                1200
ACG ATG ACC CAC CCG GAC CTG TCA ACA TGC GGA CCT CAC GAA GTC GAA CGT GAG ATT GTC GAG GCA AGT GAG GCC
Thr MET Thr His Pro Asp Leu Ser Thr Cys Gly Pro His Glu Val Glu Arg Glu Ile Val Glu Ala Ser Glu Ala 1215                                                1275
ATT ATC GCG CTT GTC CTC AGG CCG TCC GAC ACA TAC GAA GCA CCT TAT GGT GTC TGG ACC GAG GAA GCT CTG
Ile Ile Ala Leu Val Leu Arg Pro Ser Asp Thr Tyr Glu Ala Pro Tyr Gly Val Trp Ser Glu Glu Ala Leu 1320                                                1350
ACA AGA TCG GCA AGC GCT GGG CTG ACG GCA ATA CAT TGG TCG GCA GAT CCG CGA GAT CCG CGA GCC GCC
Thr Arg Ser Ala Ser Ala Gly Leu Thr Ala Ile His Trp Ser Ala Asp Pro Arg Asp Trp Ser Arg Pro Gly Ala 1365                                                1425
AAC GCG ATT GTT GAT GCA GTG CTC GAC TCG GTT CGG CCC GGT GCA ATC GTG CTG TTG CAC GAT GGG TGC CCT CCC
Asn Ala Ile Val Asp Ala Val Leu Asp Ser Val Arg Pro Gly Ala Ile Val Leu Leu His Asp Gly Cys Pro Pro 1440                                                1500
GAC GAA TCG GGA GCG CTT ACG GGT CTG CGT GAC CAA ACG CTT ATG GCG CTT TCC CGT ATC GTC CCG GCG CTG CAT
Asp Glu Ser Gly Ala Leu Thr Gly Leu Arg Asp Gln Thr Leu MET Ala Leu Ser Arg Ile Val Pro Ala Leu His 1515                                                1575
GAG CGT GGT TTT GCA ATT CGT CCA CTT CCT CCG CAT CAC TGA ACA GAC GAG AAC CCA TGT ACC TGC TTG ACA CAA
Glu Arg Gly Phe Ala Ile Arg Pro Leu Pro Pro His His .                      MET Tyr Leu Leu Asp Thr Thr 1590                                1620                                1650
CCA GCA CCG CCG CTA TCT CAA TCT TGA CCG CGC TGC TCT TGA CCG CGC TGC AAG TCC TAT ATG CTC GGC
```

```
              15                  30                  45                  60                  75
ACT TCA GGG TTC TCT  AAT AGG ACT CTG CAA  GAT TGG TAA AAT TGA  TTG TTT GGA TAA CGA  TCA TCT GCG ATA TGG
MET Pro His MET Arg  Phe Arg Gly Leu Asp  Leu Asn Leu Val Ala  Leu MET Thr Glu Arg  Lys 90                 105                 120                 135                 150
ATG CCG CAC ATG CGT  TTT AGG GGC CTA GAT  CTA AAC CTC CTC GAC  GCC CTC ATG ACC GAG  CGC AAG
MET Pro His MET Arg  Phe Arg Gly Leu Asp  Leu Asn Leu Val Ala  Leu MET Thr Glu Arg  Lys 165                 180                 195                 210                 225
CTC ACG GCC GCA CGC  ATC AAC CTC AGT CAA  CCC GCC ATG AGC GCT  ATC AGC GCC CTC CGC  ACC TAT
Leu Thr Ala Ala Arg  Ile Asn Leu Ser Gln  Pro Ala MET Ser Ala  Ile Arg Ala Leu Arg  Thr Tyr 240                 255                 270                 285                 300
TTC GGC GAC GAG CTG  TTT TCC ATG CAG GGC  CGC GAA CTT ATC CCC  ACA CCG CGT GCC GAG  GCA GCC
Phe Gly Asp Glu Leu  Phe Ser MET Gln Gly  Arg Glu Leu Ile Pro  Thr Pro Arg Ala Glu  Ala Ala 315                 330                 345                 360                 375
GTG CGC GAC GCC TTA  CTC CAC ATT CAG CTT  TCC GTC ATT GCC CGG  CCA GAT CCA CTA AAC  CCG CCC
Val Arg Asp Ala Leu  Leu His Ile Gln Leu  Ser Val Ile Ala Arg  Pro Asp Trp Asp Ser  Asp Arg 390                 405                 420                 435                 450
CGT TTC AGG ATC ATC  CTT TCC GAT TTC ATG  ATA CTT CTA TTC TTT  GCC AGG ATC GTC GAA  CTT CAG
Arg Phe Arg Ile Ile  Leu Ser Asp Phe MET  Ile Leu Val Phe Phe  Ala Arg Ile Val Glu  Leu Gln 465                 480                 495                 510                 525
GCT CCC GGC GTC AGC  TTC GAG TTG CTG CTG  CCT CTC GAT GAT GAT  CCT CAT GAG CTT CTC  CGG CCG
Ala Pro Gly Val Ser  Phe Glu Leu Leu Leu  Pro Leu Asp Asp Asp  Pro His Glu Leu Leu  Arg Arg 540                 555                 570                 585                 600
TTT CTG ATT TTT CCA  GAC GTC TCG AGC GCG  CAT CCC AAA TTC TTC  GAC CAG GCA CTC CTC  TGC
Phe Leu Ile Phe Pro  Asp Val Ser Ser Ala  His Pro Lys Leu Phe  Asp Gln Ala Leu Leu  Cys
```

```
                615              630              645              660              675
CTC GGC TGC CCC AAC AAG CTA TTG GGG AAC ATC TCC TTC GAG ACC TAT ATC TCC ATG CGC CAT CTT CCA
Val Gly Cys Pro Asn Lys Leu Leu Gly Asn Ile Ser Phe Glu Thr Tyr Ile Ser MET Gly His Val Ala 690              705              720              735              750
GCC CAG TTC GGA CGA GAA ATC AAG CCC TCC GTC GAG CAA TGG CTA TTG CTT GAG CAC CGC TTC AAT AGG CGT ATC
Ala Gln Phe Gly Arg Glu Ile MET Lys Pro Ser Val Glu Gln Trp Leu Leu Leu Glu His Gly Phe Asn Arg Arg Ile 765              780              795              810              825
GAG CTT GTT GTG CCA GGT TTT ACC TTA ATC CCA CGC CTA TTG TCG GGT ACT AAC CGA ATA CCA ACT TTA CCA TTG
Glu Leu Val Val Pro Gly Phe Thr Leu Ile Pro Arg Leu Leu Ser Gly Thr Asn Arg Ile Ala Thr Leu Pro Leu 840              855              870              885              900
CGT TTG GTT AAA TAT TTC GAA CAA ACG ATA CCA CTG CGC ATA GTC ACA TCT CCG CTG CCC CTC TTT TTC ACT
Arg Leu Val Lys Tyr Phe Glu Gln Thr Ile Pro Leu Arg Ile Val Thr Ser Pro Leu Pro Leu Phe Phe Thr 915              930              945              960              975
CAA GCT ATC CAG TGG CCC CCC CTT CAC CAA AAC ATT TGG CGG TTG CGG GAG ATA CTG TTG CAA GAG
Gln Ala Ile Gln Trp Pro Pro Leu His Gln Asn Ile Trp Arg Leu Arg Glu Ile Leu Leu Gln Glu 990              1005             1020             1035             1050
GCG TCG CGC ATT GAT CCT CAG TCG GAC ACC TGT TAG ACG TTG CCA AGA GCC TTA ACT TGC ATG TTG ATC AAG AAC
Ala Ser Arg Ile Asp Pro Gln Ser Asp Thr Cys .

1065
TCC TCG CTT TTC TCC GGT GCT T
```

FIG.—1B continued

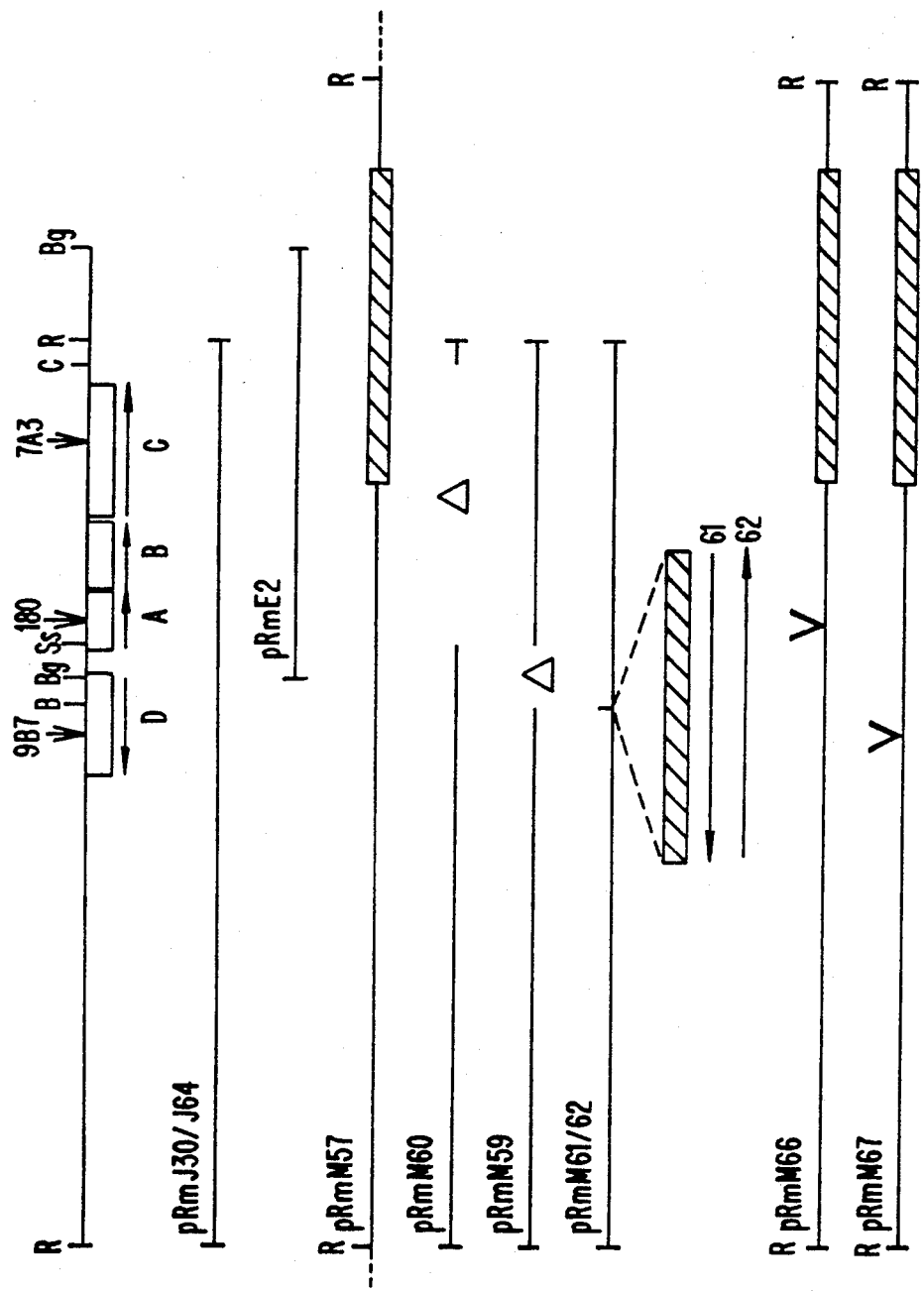
FIG.—2

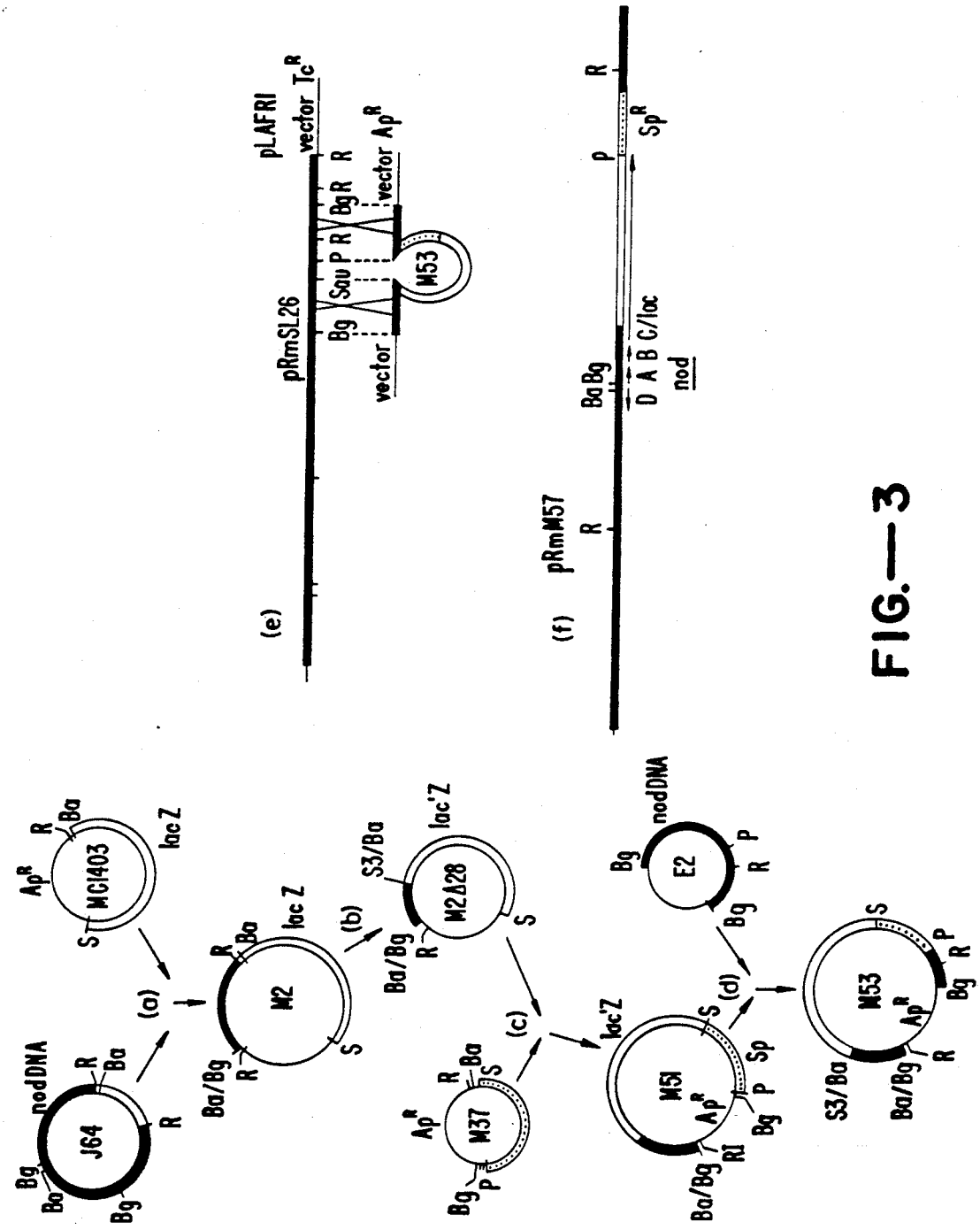
FIG.—3

BACTERIAL PROMOTERS INDUCIBLE BY PLANT EXTRACTS

FIELD OF THE INVENTION

This invention relates generally to controlling the delivery to plants of pesticides, growth regulators, nutrients and other agents and, more particularly, to the development of a multi-component system for transcriptional initiation regulatory control of one or more structural genes in bacteria.

BACKGROUND OF THE INVENTION

The ability to isolate and manipulate nucleic acid sequences encoding polypeptides has greatly increased research efforts into improved means for expressing these proteins in both natural and foreign hosts. Due to their ready availability, easy manipulation, and economy of use, unicellular microorganisms (e.g., bacteria and yeast) have been studied and utilized extensively for the production of such polypeptides.

When employing unicellular organisms, it is desirable to enhance the production of the polypeptide product of interest, with minimal interference on the production of other materials necessary for the cell's growth and/or maintenance. This permits maximal production of the desired products over an extended time period, with concomitant cost benefits. For these and other reasons, methods have been devised for selectively enhancing polypeptide expression in bacterial hosts.

One technique has been to couple the protein of interest to a promoter that is recognized by the host and allows for controlled regulation of efficient transcription of the gene encoding the polypeptide. Frequently, a "high-producing" host promoter is used, i.e., one associated with the natural production of a polypeptide that formally comprises a high percentage of the total protein of the host (or at least that provides a high transcription turnover rate). Typically, inducible promoters are preferred, because they permit expression of the gene under control in the presence of an inducing agent.

Generally, inducible promoters are useful only to the extent that the regulatory circuit and its components are understood and further to the extent that the components do not cross-react with other promoter or suppressor systems. Thus, well-defined and highly specific regulatory circuits, particularly promoter and regulatory components, have significant utilities.

In parallel to the above, the expanding research base concerning plant and related bacterial physiology has resulted in the development of various new agents active in plant nutrition, growth and protection (e.g.,pesticides, growth regulators, including hormones, herbicides, etc.). Presently, for crops such new agents (as well as those previously developed) are usually applied by spraying or irrigating the materials on most, if not all, of the field where the crops are grown. Frequently, as the agent need only interact with a certain portion of the plant (e.g., the roots) to be effective, this bulk application results in substantial waste. Also, in some cases, bulk application can actually prove to be harmful, when, for example, pesticide levels surpass safe limits.

The ability of certain bacteria in the gram-negative group Rhizobium to form nodules on the roots of plants, has provided a new potential avenue for selectively introducing agents into plants. The bacteria invade the roots, multiply and eventually inhabit cells of the nodules as intracellular symbionts. This invasion capability for Rhizobium essentially extends through one family of plants, the Leguminosae, which includes such important crops as soybean, alfalfa, clover, beans, garden peas, peanuts, cowpeas, etc. However, to effectively utilize this capability for introducing additional desired agents requires increased understanding of the genetics of nodulation.

Thus, there exists a significant need for additional and improved means for applying agents to crops and other plants of interest. Further, there exists a significant need for the development of defined and specific inducible promoter systems for use in bacteria such as those capable of forming root nodules. The present invention fulfills these needs.

DESCRIPTION OF RELEVANT LITERATURE

Nodulation (noc; genes, which certain bacteria require for invasion and stimulation of nodule formation on plants, have been identified in and cloned from several Rhizobium species. Long, S. et al., (1982) Nature 298: 485–488; Hombrecher, G. et al., (1983) EMBO J. 2: 947–952; Schofield, P. et al., (1983) Mol Gen. Genet. 192: 459–465; and Kondorosi, E. et al., (1984) Mol. Gen. Genet. 193: 445–452. The host specificity of the nodulation genes of various Rhizobium species is known, but a number of nod mutants are subject to inter-species complementation. Dusha, I. et al., (1981) Mol. Gen. Genet, 184: 318–325; Fisher, R. et al. (1985) Appl. Env. Microbiol. 49:1432–1435; and Djordjevic, M. et al., (1985) Plant Mol. Biol. 4: 147–160. It has been reported that certain bacterial characteristics are altered by exposure to plants or plant exudates. See, Dazzo, F. and Hubbell, D. (1982) in Nitrogen Fixation 2, ed. Broughton, W. (Oxford University Press), pp. 275–309; Vincent, J. (1974) in *Biology of Nitrogen Fixation* ed. Quispel, A. (North-Holland Press, Amsterdam), pp. 265–341; and Bhagwat, A. and Thomas, J. (1982) Appl Env. Microbiol. 43: 800–805. Also, an E. coli regulatory system has been described in which a regulatory gene is transcribed divergently from the gene set it regulates. Lee, N. et al. (1981) Proc. Natl. Acad. Sci. U.S.A. 78:752–756.

SUMMARY OF THE INVENTION

Novel DNA segments of various sizes and constructs are provided for the production of polypeptides, the genes of which are under control of a divergent Rhizobium nodulation gene transcriptional initiation regulatory region that is responsive, in one direction, to plant exudate in the presence of a nod D gene product. The regulatory region may be isolated from a *Rhizobium meliloti* megaplasmid, and when utilized proximate to foreign DNA fragments, is capable of controlling the expression of genes encoded by such fragments.

In one embodiment, a DNA segment of the present invention includes two divergent promoters; one that promotes production of a nod D gene product, which product acts in conjunction with plant exudate and a second divergent promoter to control the transcription of a second gene of interest in opposite orientation and on the opposing strand to the nod D gene. The second gene may be any of a variety of structural genes, including those encoding metallothionein, siderophores, herbicides, plant hormones or the like. In another embodiment, the nod D gene may be provided in trans or on a different DNA segments. In both constructs, the nod D gene product retains transcription initiation control over other genes of interest inserted downstream from the second divergent promoter.

This multi-component transcriptional initiation regulatory region provides improved means to control the expression of polypeptide structural genes and other DNA sequences. Moreover, the DNA constructs of the present invention provide improved means for controlling the delivery of agents to plants. Other features and advantages of the invention will become apparent from the following detailed description, which describes, in conjunction with the accompanying figures and by way of example, the present invention.

BRIEF DESCRIPTION OF THE FIGURES

FIG. 1 indicates the nucleotide and putative amino acid sequences of the *R. meliloti* 1021 nodulation genes and transcriptional initiation regulatory region of the present invention. In FIG. 1A, the nucleotide sequence and amino acid translation of nod A (begin at base 302) and nod B (begin at base 889) are shown. Inverted repeats 1A, 1B (....) and 2A, 2B (----) are designated. The potential start site for nod D is indicated at base 36 of the sequence, with Nod C beginning at base 1557. FIG. 1B indicates the nucleotide sequence and amino acid translation of nod D. The proposed start site for nod D is at bp 85-87.

FIG. 2 illustrates the construction of pRmM57, the plasmid containing a nod C-lacZ fusion.

FIG. 3 depicts the restriction map of the *R. meliloti* nod DABC region (top line), as well as various plasmids and fusions of the present invention.

DESCRIPTION OF THE SPECIFIC EMBODIMENTS

In accordance with the present invention, novel DNA segments are provided that include a Rhizobium nodulation gene transcriptional initiation regulatory region that is responsive to plant exudate in the presence of a nod D gene product. The DNA segments containing the region can be about 1500 bp or less, preferably about 500 bp or less, and typically contain a substantial portion of the 266 bp region shown in FIG. 1 between the nod D and nod A genes. The region includes two divergent promoters, i.e., promoters that can initiate transcription and expression of genes fused to them, where the genes are on opposite DNA strands and in opposite orientation. The region acts to promote the expression of a first gene product in one direction, and when that gene is a nod D gene, the second gene on an opposing DNA strand is then promoted only in the presence of plant exudate. Alternatively, the gene product encoded by the nod D structural gene may be added separately to the divergent promoters, such as by providing the nod D structural gene in trans, yet the promoter system remains inducible for the production of the second gene with the addition of plant exudate.

When a DNA segment of the present invention is fused to a structural gene of interest and then ligated in an extrachromosomal element, which in turn is used to transform a bacterium, the bacterium can be introduced into a field and yet the structural gene will only be produced when the bacterium associates with roots of plants. Preferably, the DNA segment will become incorporated into the genome of the bacterium, which can improve the degree of control over transcriptional initiation of the structural gene and will improve the stability of the construct.

The invasion of leguminous plants by Rhizobium is the first step in the establishment of nitrogen-fixing, symbiotic root nodules, the development of which requires both bacterial and plant genes. Bacterial nodulation loci have been identified in and cloned from several fast-growing Rhizobium species and have been mapped to large symbiotic plasmids and linked to nitrogen-fixation genes. In *R. meliloti* 1021, a symbiont of alfalfa, a cluster of four nod genes has been characterized. The nod D gene specifying a protein of about 308 amino acids, is transcribed divergently from an operon of three genes, nod ABC (see FIG. 1). These four *R. meliloti* 1021 genes are functionally conserved with nod genes of other fast-growing Rhizobium strains, including *R. trifolii* and *R. leguminosarum*.

The nod A open reading frame (ORF) specifies a protein of about 197 amino acids, while the nod B ORF specifies a protein of about 217 amino acids. The start site for the nod C gene is located about 31 bp 3' to nod B (see FIG. 1B). The nod A and nod B open reading frames show an overlap of four base pairs (A (TG) A). While the translational start site of each gene cannot be determined from sequence data alone, the potential overlap of nod A and nod B suggests the possibility of translational coupling of these two genes.

The nod D gene reads in the opposite direction for 308 amino acids. It therefore appears that nod D and nod A are transcribed from divergent promoters in the 250 bp plus segment separating nod D and nod A. Two regions with inverted repeats were found in the nod D-nod A region (FIG. 1A). Segment 1A lies 15-27 bp upstream from nod D; it is conserved at 11/12 bp with 11/13 of segment 1B, 100 bp upstream from nod A. Segments 2A and 2B lie 5' to nod A by 70 bp, and would permit a hairpin to form in which an 11 bp stem has only one mismatch. The position of this potential hairpin upstream from nod A would be consistent with a role in transcription control.

As shown in FIG. 1A, assuming the translation initiation site of nod D occurs with the met residue coded by the ATG at nucleotides 85-87 in FIG. 1B, there exists a 266 bp region separating the nod D and nod A genes. Thus, a DNA segment containing the divergent promoters of the present invention, will generally include at least about 50-200 bp from the transcription start site, and typically be under 1,500 bp, usually under about 300 bp. When the nod D gene (or portion thereof) is fused in its natural position to the promoter, the DNA segments of the present invention will be increased by at least about 1-200 bp, more usually about 500 bp, and generally by about 1000 bp. Similar increases will result in additions of all or part of the nod A, nod B, nod C on other genes.

As noted above, in an appropriate host the nod D gene is produced under control of the regulatory region. When a second gene is fused on the opposing strand and in the opposite direction from the nod D gene, the expression of this second gene is then influenced by the presence of plant exudate. Thus, the DNA segment of the present invention can serve as a regulatable, multi-component transcription initiation regulatory region.

These DNA segments also have utility in the construction of novel bacterial strains that produce substances only on contact with plants or their exudates. By transforming bacteria with DNA segments containing the regulatory region of the present invention fused to DNA sequences from various sources, the bacteria can, at appropriate times, express polypeptides capable of providing plants with desirable characteristics.

Thus, bacteria can be induced to assist plants to exhibit resistance against invasion by foreign organisms, such as pathogens, nematodes, insects, etc., by providing polypeptides that act either alone or with their products or other agents as toxins against such pests (e.g., *Bacillus thuringiensis* endotoxin protein). These agents may also protect against chemical imbalances or excess toxic chemicals, and the like. The agents can control amino acid levels in the plants, and generally increase or decrease nutrient levels. Further, the bacteria can contain genes encoding agents having growth control activity over the plants or portions thereof (e.g., fruit). Indeed, selective herbicidal proteins or proteins useful in herbicide detoxification (such as against residual atrazine) could also be produced.

Genes encoding polypeptides capable of inducing herbicidal resistance in plants have been cloned and introduced into plants. These include the bacterial genes encoding for chlorsulfunon and sulfmeturon resistance, as well as the glyphosate resistance gene from Salmonella. If desired, these and various additional genes may be provided in a polycistronic form. The particular structural gene inserted as an agent is not critical to this aspect of the present invention, and any polypeptide or protein of interest may be prepared employing these constructions as described herein.

Typically, the structural gene will be at least about 60 bp, not more than about 10 kbp, usually not more than between about 1000 and 3000 bp. Included with the structural gene may be non-coding flanking regions, the 5' flanking region normally being relatively short (less than about 30 bp), while the 3' flanking region may be extended, usually not exceeding about 500 bp. Thus, the structural gene fragment will usually include the translational stop codons for proper termination of amino acid chain extension.

The bacteria containing the DNA constructs of the present invention can be applied to plants in any of a variety of means well-known to those skilled in the art. Importantly, however, because the polypeptide genes will only be expressed in the presence of plant exudate, unwanted production of such substances will be minimal. Moreover, by carefully choosing the bacteria, it is possible to limit the production of the substance to a selected portion of the plant. Thus, for example, as certain bacterial strains (e.q., Rhizobium) may bind at enhanced levels to roots, the substance under control of the promoter will generally first act on the infected roots, with or without nodule formation.

If desired, the DNA segment may contain a variety of additional DNA sequences capable of providing regulatory functions. These include capping sequences, signals involved with further enhancing or regulating transcription, an initiation site or codon, and portions of coding regions, such as leader sequences or the like. In this manner, one can provide a segment having a plurality of functions and capabilities.

Likewise, extending downstream from the promoters may be a wide variety of flanking sequences, providing numerous functions. One can provide for a cohesive ends or butt ends to the promoter fragment, to enable ready ligation to other DNA sequences. Also, linkers having specified restriction sites can be ligated to the promoter to further simplify the addition of additional DNA sequences.

Conveniently, the DNA segments of the present invention may be integrated into the bacterial genome and incorporated into extrachromosomal elements, such as bacterial plasmids. A preferred type of plasmid includes those able to replicate in many bacterial groups (e.g., incompatability group P). The replication systems may be high or low copy number, depending on the effect the construct has on viability of the host. Often the DNA segments will be inserted into an appropriate shuttle vector capable of replication and selection in one host, but capable of transfer to another host by way of conjugation or other standard techniques.

Numerous additional capabilities may be introduced into the extrachromosomal element to provide for various desirable traits. Usually, markers are provided for the host in which the construct is to be introduced to provide for selection pressure. This can be used to determine if the extrachromosomal element has been incorporated into the host and to ensure that the host retains the construct after the initial introduction period. Markers may include biocidal resistance, such as antibiotic resistance, complementation to prototrophy, or the like. One or more markers may be desirable, depending upon the need for and the desirability of having different selective pressures.

The following examples are offered by way of illustration and not by way of limitation.

EXPERIMENTAL

All DNA manipulation were performed according to standard procedures. See, Maniatis, T. et al. (1982) Molecular Cloning, Cold Spring Harbor Laboratory. *R. meliloti* 1021 is a streptomycin-resistant derivative of SU47 (see, Meade, H. et al., (1982) J. Bacteriol. 149: 114–122). *R. meliloti* 1027 and 1126 are readily available nodulation deficient mutant strains.

A nodulation gene region in *Rhizobium meliloti* was initially cloned and localized to an 8.7 kb EcoRI fragment from the pSym megaplasmid as described in Long, S. et al., (1982) Nature 298:45–48 (which is incorporated herein by reference), as follows. A clone bank of wild-type *R. meliloti* 1021 DNA was constructed by partial digestion of total DNA with EcoR1 and insertion into the EcoRl site of pLAFR. The plasmid pLAFR is a low copy number broad host range vector of about 21.6 kb, which confers tetracycline resistance and can be mobilized from *E. coli* into *R. meliloti* by the specially constructed complementing plasmid pRK2013 (Figurski, D. and Helinski, D. (1979) P.N.A.S. U.S.A. 76:1648–1652). The *R. meliloti*-pLAFRl ligated DNA mix was packaged in phage lambda heads as described in Hohn, B. Meth. Enzym. (1979) 68:299–309. The mean insert size was about 23.1 kb, and the bank contained approximately 15,000 independent plasmids.

The pLAFRl clone bank, maintained in *E. coli* strain HB101, was conjugated into *R. meliloti* strains 1027 and 1126 in a tri-parental mating as described by Ruvkun, G. and Ausubel, F. (1981) Nature 289:85–88. Tetracycline-resistant *R. meliloti* ex-conjugants were scraped together in batches of 200–300 colonies, onto a group of five to eight aseptically-grown alfalfa plants, each grown in a separate test tube on nitrogen-free nutrient agar. The plants were observed after four weeks for the presence or absence of root nodules.

In one conjugation, three inoculation mixtures produced no nodules on host plants, while inoculation with two additional batches of ex-conjugants resulted in nodule formation on roots of every plant. Essentially the same result was found with a second conjugation, except for the formation of one apparently aberrant nodule on a plant in group B-5, which was probably due to a Nod+ revertant of strain 1027. Parental controls (plants inoculated with 1126 or 1027) were free of nodules.

To determine whether nodule formation by these groups of ex-conjugants was due to the presence of a cloned gene that complemented a nod lesion, the nodules were removed from the plants and analyzed as follows.

The removed nodules were washed and 0.5% SDS and 10M NaCl, submerged for five minutes in 70% ethanol, washed twice in sterile H₂O and squashed using a sterile glass rod into 1.0ml of a solution containing 12% sucrose, 50mmol Tris, 5mmol EDTA, and 10mmol NaCl, all at pH 7.5. Dilutions of this mixture were mixed on LB plates (10g tryptone, Difco), 5g yeast extract, 5g NaCl, and 5g agar, all at pH 7.2. Single colonies were purified and tested for tetracycline resistance. Nodulated plants were assayed for nitrogenase activity, using the acetylene reduction method described in Ruvkun, G. and Ausubel, F. (1981) Nature 289:85-88 (which is incorporated herein by reference).

The nodules typically yielded a mixture of *R. meliloti* cells containing pLAFR1 clones no plasmid. Also, in some nodules, two types of plasmids were found. One type showed no consistent pattern; however, the second was always a particular plasmid, designated pRmSL26. This suggested that clone pRmSL26 contained one or more genes used in nodulation. When this plasmid was placed in the Nod− 1027 and 1126 strains, they became Nod+ and provided the same level of nitrogenase activity in plants as compared to a wild type strain.

To prepare fragments of clone pRmSL26, the plasmid was first CsCl gradient-purified. The DNA was then digested with EcoRI, ligated with pBR325 and transformed into *E. coli* LE392, selecting for ampicillin resistance and screening for insertional inactivation of chloramphenacol resistance. Transformation of *E. coli* with 0.7 micrograms of ligated DNA yielded $6.6 \times 10^5$ transformants that were both ampicillin and tetracycline resistant, 15% of which were also chloramphenicol resistant. Clones containing the 8.7, 3.8, 3.5, 1.8, 1.25 and 0.6kb EcoRI subfragments of pRmSL26 were identified by rapid plasmid screening of the resistant transformants. These subclones were named pRmJ1 through pRmJ6, respectively. The 8.7kb EcoRI insert of pRmJ1 was also subcloned into pLAFR1 (pRmJ30).

Two methods for site-directed mutagenesis of the 8.7-kb EcoRI fragment were utilized, both references are incorporated herein by reference. In one, Tn5 insertions in pRmJ30 were generated and mapped in *E. coli*, and mutated plasmids were conjugally transferred into *R. meliloti* and homogenotized by a method exploiting plasmid incompatibility (Ruvkun, G. and Ausubel, F. (1981) Nature 289:85-88. The second approach entailed generating Tn5 insertions in pRmJ1, which were conjugally transferred into *R. meliloti* and homogenotized by plasmid host-range restriction (Comai, L. et al. (1983) Plasmid 10:21-30). This latter method was generally inefficient because of background transposition of Tn5 before homogenotization.

A total of 81 Tn5 insertions were mapped and homogenotized into the 8.7kb ECORI fragment. Of these mutations, 39 resulted in an altered nodulation phenotype. Transposon Tn5 insertions throughout the left (nif-distal) portion of the 8.7kb fragment had no effect on nodulation. In contrast, insertions in a region extending between 0.5 and 4.0kb from (nif-proximal) EcoRI site produced a Nod− phenotype.

To determine the position of potential coding regions within the 8.7 kb Nod fragment, portions were sequenced by both chemical cleavage (Maxam, A. and Gilbert, W. (1980) Methods in Enzymol., 64:499-560) and dideoxy termination (Sanger, F., et al. (1977) *Proc. Natl. Acad. Sci. U.S.A.*, 74:5463-5467) methods. Tn5 was used to gain access to certain segments for which convenient restriction sites had not yet been located. A 17-nucleotide segment, 3'-GTTCATCGCAG-GACTTG-5', which extends from 15 to 31 bases from the ends of Tn5, was used as a primer for dideoxy chain termination DNA sequencing.

The sequence analysis of the EcoRI fragment revealed open reading frames corresponding to nod A, nod B and nod C genes encoding 196, 217, and 426 amino acids, respectively. The contiguity of these three genes suggests that they constitute an operon. The nod A and nod B opening reading frames show an overlap of 4bp [A(TG)A]. This suggests the possibility of translational coupling of the two genes.

The sequence of the nod C gene is highly conserved in *R. meliloti* 41 (99% amino acid homology) and *R. leguminosarum* 248 (71% amino acid homology). Multiple methionine codons exist in the N-terminal portion of the nod C gene. Translation initiation at the first methionine would yield an amino acid terminus with signal peptide character, although the presence of a negatively-charged amino acid differs from the typical prokaryotic signal sequences commonly found. The amino acid sequence of nod C revealed two domains of contrasting hydropathy, the C-terminal half being more hydrophobic than the N-terminal half. This is consistent with the finding that two classes of nod C mutants show differing apparent complementation of Nod− mutants from a different bacterial strain (*R. trifolii*).

The nod D gene reads for 308 amino acids in the opposite direction from the other three nod genes. Thus, the nod A and nod D genes are transcribed from divergent promoters in the 266bp segment separating the two genes.

To measure the activity of nodulation loci in *R. meliloti* strain 1021, various translational gene fusions were constructed. Plasmid constructions were generally carried out by the method of Crouse, G., et al. (1983) Methods in Enzymol. 101:78-89. First, a translational fusion of the *R. meliloti* nod C N-terminal peptide to *E. coli* lacZ was constructed, and flanking sequences added as shown in FIG. 2. Briefly, the 3.6kb EcoRI to BamHI fragment of pRmJ64 was cloned into pMC1403 cut with EcoRI and BamHI to produce pRmM2. This plasmid was partially digested with Sau3A in the presence of ethidium bromide, and then digested to completion with BamHI. The resulting variable length molecules were ligated at low concentration, forming derivatives of pRmM2 with deletions bounded on one end by a Sau3 site and on the other by a BamHI site. The ligation mixture was transformed into LE392, grown selectively in liquid, plasmid-prepped, and then transformed into MC1061. Ampicillin resistant colonies were screened on X-gal medium and faint blue colonies, in which the incomplete lacZ gene from pMC1403 was fused to any translation start site, were picked. Plasmids from these colonies were isolated and mapped. A fusion that mapped in nod C, pRm2 delta 28, was linked to a selectable marker by recloning the EcoRI-SalI fragment (containing the Rhizobium genes and the fusion) into a plasmid containing spectinomycin resistance in a polylinker, to produce pRmM51. Thereafter, the BglII-PstI fragment from pRmE2 was cloned into pRmM51, yielding pRmM53, which has homology to *R. meliloti* on both sides of the lacZ-spectinomycin resistance fragment. Plasmid pRmM53 was forced to recombine with pRmSL26 by mating both plasmids into C2110 and selecting for spectinomycin resistance. A plasmid in which the resolution of the cointegrate had converted nod C into a nod C-lacZ fusion was isolated by screening the spectinomycin resistant colonies for tetracycline resistance and ampicillin sensitivity. This plasmid, pRmM57, was transformed into MC1061, and its restriction map was confirmed.

LacZ was also joined in-frame to *R. meliloti* nod D by a one-step procedure in which the lacZ-SpR cartridge of pMC931 Sp was inserted into the unique BamHI site of pRmJ30 in both orientations. The direction in which nod D is fused in frame to lacZ is designated pRmM61, while the opposite direction is designated pRmM62 (see FIG. 3).

Plasmid pRmM66 was constructed by conjugated plasmids pRmM57 and pRmJ27 into C2110, selecting spectinomycin and kanamycin resistance, and screening for ampicillin sensitivity. It contains the nod D-lacZ fusion and a Tn5 insertion in nod A. Plasmid pRmM67 was constructed by using the same scheme to recombine the nod C-lacZ fusion on pRmM53 into pRS9B7 (a nod D::Tn5 derivative of pRmJ30).

Plasmid pRmE43 carries the nod D structural gene inserted into a broad host range (inc-P) expression vector, pTE3. These were constructed as follows: pRK290 (Ditta et al, 1980, Proc. Natl. Acad. Sci. U.S.A. 77:7347-7351) was digested with EcoRI and the ends were filled in with Klenow enzyme. Into this site was ligated a 670 bp PvuII fragment from the expression vector pAD10. The vector pAD10 is derived from pAD7 (Das et al., Proc. Natl. Acad. Sci. U.S.A. (1983) 80:2879-2883, which is incorporated herein by reference), which contains a *Salmonella typhimurium* trp promoter inserted into the HindIII site of pUC8 and oriented so the transcription reads across a downstream polylinker. In addition, it contains the *E. coli* rpoC ; terminator (Das et al., J. Biol. Chem. (1982) 257:8795-8798, which is incorporated herein by reference) inserted into the EcoRI site on a 240 bp restriction fragment. The downstream EcoRI site was removed by filling in with Klenow fragment so that the vector has unique polylinker sites for PstI, SalI, BamHI, SmaI and EcoRI, all located between the trp promoter and the rpoC terminator. Into the polylinker of pTE3 was inserted a fragment of about 1.3 kb containing all the *R. meliloti* DNA from a SstI site to a BclI site, and which therefore contained all of the nod D structural gene plus upstream DNA segments. The resulting plasmid, pRmE43, therefore bears *R. meliloti* nod D inserted in the correct orientation downstream from the trp promoter.

Strain M57, carrying the nod C-lacZ fusion on the megaplasmid, was constructed by conjugating plasmid pRmM57 into strain TJ6B2, which has a Tn5 insertion (*7A3) in the megaplasmid copy of nod C. The pRK290 plasmid pRmM57 was then excluded from this strain by introducing incompatible plasmid pR751. Trimethoprim and spectinomycin products of this conjugation were found to be tetracycline and kanamycin sensitive, indicating loss of the pRmM57 vector with concomitant marker exchange of the nod C-lacZ fusion. Strain M61, carrying the nod D-lacZ fusion, was produced by marker exchange of pRmM61 into the megaplasmid by a similar procedure.

Plant exudate was prepared as follows. Plant seeds were sterilized by soaking in ethanol for 30 min. and full strength chlorine bleach for an additional 30 min. The seeds were rinsed, then imbibed overnight 2-3 volumes of water to yield the seed wash fraction. Root washes were collected 3 hr. to several days after addition to the sprouted seeds. Both seed and root washes were sterilized by boiling or filter sterilization immediately after collection and were tested for the presence of bacteria by plating on rich bacterial media. Production of active exudates did not require presence of bacteria, and exudates exposed to bacteria rapidly lost activity.

The assays for beta-galactosidase were performed as described in Miller, J., (1972) Experiments in Molecular Genetics, Cold Spring Harbor (which is incorporated herein by reference), with the following modifications. All volumes were scaled down by a factor of 0.75 so that the assays could be performed in 1.5 ml microfuge tubes. The cells were permeabilized with 100 microliters chloroform and 50 microliters SDS. After the reactions were terminated, they were spun in a microfuge for about 5 min. prior to measuring the OD at 420 and 620 nm (550 nm was assumed to be 0). The cultures were grown to early log phase in flasks and transferred to tubes in 2.5ml aliquots for induction. Four tubes were assayed for each condition and each strain data point. Induction was performed by adding 1/10th volume of root or seed wash to early log phase cultures 3 hr. before the samples were assayed. The results of the assays are shown in Table I.

TABLE I

| | Strain | Beta-galactosidase Units | |
|---|---|---|---|
| | | −Inducer | +Inducer |
| 1. | 1021 | 2 | 2 |
| 2. | 1021 (p26) | 2 | 2 |
| 3. | 1021 (pRmM57) | 15 | 475 |
| 4. | 1021 (pRmM66) | 24 | 20 |
| 5. | 1021 (pRmM61) | 750 | 810 |
| 6. | 1021 (pRmM62) | 5 | 7 |
| 7. | 7125 (pRm57) | 5 | 10 |
| 8. | TJ7A3 (pRmM57) | 15 | 450 |
| 9. | 7125 (pRmM61) | 67 | 63 |
| 10. | TJ9B7 (pRmM61) | 815 | 750 |
| 11. | JM61 | 50 | 50 |
| 12. | JM57 | 2 | 8 |
| 13. | JM61 (pRmSL26) | 50 | 47 |
| 14. | JM57 (pRmSL26) | 3 | 55 |
| 15. | JM57 (pRmM60) | 2 | 43 |
| 16. | JM57 (pRmM59) | 2 | 4 |
| 17. | JM57 (pRmM9B7) | 2 | 4 |
| 18. | Rm1021 (pRmM67) | 12 | 13 |
| 19. | JM57 (pRmE43) | 4 | 110 |

As shown in Table I, basal beta-galactosidase activity of the parent *R. meliloti* strain 1021 is low, and is not affected by plant extract or by extra copies of the wild type nod genes on plasmid pRmSL26. Strain 1021 carrying the nod C-lacZ protein fusion on pRmM57 has higher basal levels, and shows 30-fold induction of beta-galactosidase activity in the presence of plant exudate. This exudate could be obtained from alfalfa seeds or aseptically-grown roots by soaking the plant material in water.

Plasmid pRmM66 bears the same nod C-lacZ fusion as pRmM57, but also contains a Tn5 insertion in nod A. The uninduced enzyme activity for this strain in intermediate and does not increase upon treatment with plant extract. This suggests that nod ABC may be a transcriptional unit and that sequences upstream from nod A are required cis to nod C for regulation.

In a second gene fusion, lacZ was fused in-frame to the first 88 amino acids of nod D, generating pRmM61. Strains containing this plasmid displayed high levels of beta-galactosidase activity independent of added plant extract, in contrast to the behavior of the nod C-lacZ protein fusion in pRmM57. LacZ inserted in the antisense direction on pRmM62 had low levels of enzyme activity in the presence or absence of plant exudate.

R. meliloti strain 7125 has the R. meliloti megaplasmid, but deleted for about 220kb, including the nod DABC and nifHDK genes. The induction seen in Rm1021 (pRmM57) was not observed in Rm7125 (pRmM57), but was found in a nodC::Tn5 strain, TJ7A3 (pRmM57). The nod D-lacZ fusion on plasmid pRmM61 expressed markedly lower activity in the deleted strain 7125 background, but the level of nod D-lacZ expression was unchanged in nod D::Tn5 strain, TJ9B7 (pRmM61) This suggests that neither nod C nor nod D requires its own product for high level expression but that both may require sequences deleted in 7125 and not complemented by pRmSL26.

When the nod D-lacZ fusion was marker exchanged into the R. meliloti megaplasmid (RmM61), betagalactosidase activity was substantially reduced (50 units) and was still unaffected by plant exudate A comparable nod C-lacZ fusion in the genome (RmM57) . showed lower uninduced activity and the amount of induction by plant exudate was greatly reduced, only 2-4 fold above background. Extra copies of cloned nod gene DNA on pRmSL26 or pRmJ30 were introduced into Rm57 and RmM61, the marker exchanged lacZ fusions. Expression of the megaplasmid nod D-lacZ fusion showed no response to additional plasmid borne copies of the nod gene region. However, strain M57 carrying pRmSL26 or pRmJ30 (data not shown) showed a substantial increase in lacZ activity in response to plant exudate. If the introduced nod gene clone was deleted for nod ABC (pRmM60), then response of the megaplasmid nod C-lacZ protein fusion to plant exudate was still high. However, if the cloned nod gene segment carried a nod D-nod A deletion (pRmM59) or a nod D::Tn5 insertion (pRmS9B7), then the genomic nod C-lacZ fusion displayed no activity increase in response to plant exudate. A plasmid containing the nod D::Tn5 insertion in cis to the nod C-lacZ fusion (pRmM67) also displayed no (about 15 beta-galactosidase units) responce to plant exudate. These results suggest that the nod C response to plant exudate in our assay system depends on an intact, plasmid borne copy of nod D, i.e., on high levels of nod D expression.

The start site for the exudate-nod D-controlled nod A transcript probably lies within about 20 bp of the sequence 5' CCAATCTTGC AGAGTCCTAT TAGAGAACCC TGAAGTTAAT GGAAT 3', which includes base numbers 85 to 130 of the nod ABC sequence shown in FIG. 1. This was indicated to be part of the 266 bp promoter sequence by the following procedure. RNA was prepared from R. meliloti cells which had been treated with inducer. Using cloned single-strand DNA segments homologous to a DNA segment (including the translational start codon) of nod A, hybridizations were performed with the RNA and the start site of the nod A transcript was determined by primer extension from the hybridized segments and analysis of lengths of the resulting DNA's (Hudson and Davidson (1984) J. Mol. Biol. 180:1023-1051).

Thus, we have discovered that when nod D was expressed at a high level off its own promoter while on an incompability group P vector, nod C expression was increased 30-fold by exudates from plant roots or seeds grown without the presence of bacteria When the expression of nod D was low, nod C expression was unaffected by plant exudate. Expression of the fused nod D-lacZ gene depended on at least two factors the replicon on which the fusion was carried and the presence of sequences absent in Rm7125, but not complemented by pRmJ30 Its expression did not depend either on the presence of an intact nod D gene or the total copy number of the nod region Therefore, nod D is not likely to be involved in its own regulation, and further, the elevated expression of the plasmid copy of the gene is not due to titration of a negative regulatory protein by extra copies of the nod D control region. Also, induction of the nod C-lacZ fusion in response to plant exudate depended on the high level expression of nod D, even when the nod D gene was trans and under control of a separate promoter (trp-pRmE43). The nod C fusion was induced up to 30-fold in the presence of the intact plasmid copy of the nod D gene.

From the foregoing, it will be appreciated that the transcriptional initiation regulatory region of the present invention provides well-defined and specific promoter systems, which can be responsive to plant exudate. The invention also provides to those skilled in the art means for producing significant quantities of polypeptides in a bacterial host, by fusing a gene encoding the desired polypeptide to one of the transcriptional initiation regulatory segments, and then growing the host under appropriate conditions. In this manner, one can control the expression of a foreign structural gene in a bacterial host. When incorporated into a suitable bacterium, such as a Rhizobium, the expression of selected genes will be induced only when desired, such as in the presence of plant exudate. This permits the selective production of various agents useful to plants.

Although the invention has been described in some detail by way of illustration and example, it will also be apparent that various changes and modifications can be made without departing from the scope and spirit of the appended claims.

What is claimed is:

1. A process for producing a polypeptide in bacteria in association with the presence of a plant host, said process comprising the steps of:
    transforming bacteria with a structural gene encoding the polypeptide, wherein the polypeptide is fused downstream from and under control of a transcriptional initiation regulatory promoter region, the region being responsive for transcriptional initiation to a plant exudate in the presence of a Rhizobium nod D gene product;
    infecting a root of said plant host with the transformed bacteria; and
    growing the plant host, whereby said polypeptide is produced.

2. A DNA fragment of from about 50 to 1500 base pairs comprising a Rhizobium nodulation gene divergent transcriptional initiation regulatory promoter region, wherein said gene is the nod A, nod B, nod C, or nod D gene.

3. A DNA fragment according to claim 2, wherein the region is ligated into an extrachromosomal element containing DNA sequences not naturally associated with said fragment.

4. A DNA fragment according to claim 2, wherein the region is responsive to plant exudate for transcriptional initiation.

5. A DNA fragment according to claim 2, wherein the nodulation gene regulatory promoter region comprises a substantial portion of 266 base pairs.

6. A DNA fragment according to claim 5, wherein the nodulation gene is nod A.

7. A DNA fragment according to claim 5, wherein the nodulation gene is nod D.

8. A DAN fragment according to claim 2 or 5, wherein the nodulation gene regulatory promoter region is from *Rhizobium meliloti* and capable of exhibiting increased responsiveness for transcriptional initiation to plant exudate in proportion to the amount of a nod D gene product present.

9. A DNA fragment according to claim 8 wherein the nod D gene product is transcribed divergently with respect to a DNA segment under transcriptional control of the region wherein the segment is not naturally associated with the region.

10. A DNA fragment of claim 8 wherein the nod D gene product is encoded by a nod D gene on a second DNA fragment.

11. A DNA fragment according to any of claims 2, 3, or 4 further comprising a DNA segment encoding a structural gene under transcriptional control of the region, wherein the segment is not naturally associated with the region.

12. A DNA segment comprising a divergent transcriptional initiation regulatory promoter region responsive to plant exudate in the presence of one or more Rhizobium nodulation gene products, wherein said gene products comprise a nod A, nod B, nod C or nod D gene product, said region fused to a structural gene not naturally associated with said region.

13. A DNA segment of claim 12 wherein the regulator region has a DNA sequence comprising about 266 bases substantially of the sequence shown in FIG. 1.

14. A DNA segment of claim 12, wherein the nod D gene product is a *Rhizobium meliloti* nod D gene product.

15. A DNA segment of claim 12 wherein the region is capable of controlling the transcription of the nod D gene and at least one additional structural gene, wherein the nod D gene is in opposite reading frame orientation and on the opposite strand from the structural gene.

16. A DNA segment according to claim 12, wherein the structural gene encodes an agent active on a plant.

17. A DNA segment of claim 16, wherein the agent can be incorporated into the plant through root nodules.

18. A bacterium containing a DNA segment according to claim 12.

19. A plant having a nodule comprising a bacterium according to claim 18.

20. A plant of claim 19, wherein the bacterium is of the group Rhizobium.

21. A doublestranded DNA segment comprising a Rhizobium nodulation gene divergent promoter located between a nod D gene and one or more structural genes in opposite orientation to and on the opposing strand of the nod D gene, wherein the nod D gene is transcribed constitutively and the promoter is capable of initiating the transcription of the second gene in the presence of both plant exudate and an expression product of the nod D gene, wherein at least one of the structural genes is not naturally associated with said segment.

22. A DNA segment of claim 21 ligated into an extrachromosomal element containing one or more DNA sequences not naturally associated with said DNA segment.

* * * * *

UNITED STATES PATENT AND TRADEMARK OFFICE
CERTIFICATE OF CORRECTION

PATENT NO. : 5,085,588

DATED : February 4, 1992

INVENTOR(S) : SHARON R. LONG; JOHN T. MULLIGAN; THOMAS T. EGELHOFF

It is certified that error appears in the above-indentified patent and that said Letters Patent is hereby corrected as shown below:

Column 1, line 1 please insert

--This invention was made with Government support under PHS Grant No. 1R01-GM30962. The Government has certain rights in this invention.--

Signed and Sealed this

Sixth Day of December, 1994

Attest:

BRUCE LEHMAN

*Attesting Officer*            *Commissioner of Patents and Trademarks*